(12) United States Patent
Pujar (10) Patent No.: US 9,642,551 B2
(45) Date of Patent: May 9, 2017

(54) EVALUATING ATRIO-VENTRICULAR CONDUCTION IN A HEART

(71) Applicant: Chandrashekhar Pujar, Karnataka (IN)

(72) Inventor: Chandrashekhar Pujar, Karnataka (IN)

(73) Assignee: Siemens Healthcare GmbH, Erlangen (DE)

( * ) Notice: Subject to any disclaimer, the term of this patent is extended or adjusted under 35 U.S.C. 154(b) by 171 days.

(21) Appl. No.: 14/607,220

(22) Filed: Jan. 28, 2015

(65) Prior Publication Data

US 2016/0213272 A1    Jul. 28, 2016

(51) Int. Cl.
*A61B 5/04* (2006.01)
*A61B 5/0464* (2006.01)
*A61B 5/00* (2006.01)

(52) U.S. Cl.
CPC .......... *A61B 5/0464* (2013.01); *A61B 5/6852* (2013.01); *A61B 5/7264* (2013.01); *A61B 5/746* (2013.01); *A61B 2505/05* (2013.01)

(58) Field of Classification Search
CPC ..... A61B 5/0464; A61B 5/746; A61B 5/7264; A61B 5/6852; A61B 2505/05
See application file for complete search history.

(56) References Cited

U.S. PATENT DOCUMENTS 5,836,974 A * 11/1998 Christini .............. A61N 1/3702
607/5
8,761,880 B2    6/2014 Maskara et al.
2007/0197926 A1    8/2007 Danehorn et al.

OTHER PUBLICATIONS

MacDonald, Robert, et al. "A software trigger for intracardiac waveform detection with automatic threshold adjustment." Computers in Cardiology, Proceedings.. IEEE, 1989.

* cited by examiner

*Primary Examiner* — Mallika D Fairchild
(74) *Attorney, Agent, or Firm* — Lempia Summerfield Katz LLC (57) ABSTRACT

Atrial-Ventricular (A-V) condition in a heart is evaluated. Signal data sensed from the heart during an atrial stimulation of the heart is received. An Atrium-Hision (A-H) interval corresponding to an extra-stimulus event during the atrial stimulation of the heart is computed using the sensed signal data. Furthermore, a difference between the A-H interval corresponding to the extra-stimulus event and an A-H interval corresponding to a preceding extra-stimulus event is determined. Moreover, a presence of an A-H jump is automatically determined based on the determined difference.

16 Claims, 6 Drawing Sheets

EVALUATING ATRIO-VENTRICULAR CONDUCTION IN A HEART

FIELD OF TECHNOLOGY

The present disclosure generally relates to the field of abnormal cardiac rhythm detection systems, and more particularly relates to evaluating Atrio-Ventricular conduction in a heart.

BACKGROUND

The heart is the center of circulatory system of an individual. The left portions of the heart draw oxygenated blood from lungs and pump the blood to body organs to provide the organs with their metabolic needs for oxygen. The right portions of the heart draw deoxygenated blood from the organs and pump the blood to the lungs where the blood gets oxygenated.

In a normal heart, the sinuatrial node (SA node), located in high right atrium (HRA), generates electrical impulses that propagate to cardiac muscle (myocardium), thereby stimulating the cardiac muscle. The SA node has specialized cells that undergo spontaneous generation of action potentials at a rate of 100-110 action potentials ("beats") per minute, causing generation of electrical impulses. The ordered stimulation of the cardiac muscle allows efficient contraction of the heart, thereby allowing blood to be pumped throughout the body.

The sinus rhythm normally controls both atrial and ventricular rhythm. When functioning properly, electrical impulses are spontaneously generated by the SA node. Electrical impulse is propagated through the right atrium and through Bachmann's bundle to left atrium, thereby stimulating the cardiac muscle of the atria to contract. The conduction of the electrical impulse throughout the atria is seen on Electrocardiogram (ECG) of the heart as the P wave.

As the electrical impulse spreads throughout the atria, the electrical impulse travels from the SA node to Atrio-Ventricular (A-V) node, which electrically connects atrial and ventricular chambers via specialized pathways, known as internodal tracts. The A-V node delays the electrical impulse on the impulse's way to the ventricle, giving the atria time to contract first. Without the delay, the atria and ventricles would contract at the same time, and blood wouldn't flow effectively from the atria to the ventricles. The electrical impulse then enters the base of the ventricle at bundle of His and follows left and right bundle branches. The electrical impulse travels at the high velocity through Purkinje fibers at the end of the branches into the ventricles, causing stimulation of the cardiac muscle of the ventricles. The stimulation of the cardiac muscle causes the right and left ventricles to contract. The conduction of the electrical impulse through the ventricular cardiac muscles produces the QRS complex on the ECG. Thus, normal cardiac rhythm is controlled by the pacemaker activity of the SA node and the delay in the AV node.

Abnormal cardiac rhythms may occur in individuals due to improper conduction of electrical impulse through the A-V node. For example, the improper conduction of the electrical impulse is encountered due to leakage of the electrical impulse while passing through the A-V node. Typically, conduction of the electrical impulse through the A-V node is analyzed using an atrial stimulation technique. In the atrial stimulation technique, High Right Atrium (HRA) is simulated using a plurality of stimulation events. During each stimulation event, the HRA is stimulated with a series of pulses with equal pacing cycle length followed by an extra-stimulus pulse having different pacing cycle length using a pacing electrode (also known as lead). It can be noted that pacing cycle length of the extra-stimulus pulse is reduced by a pre-determined value during subsequent stimulation events.

For each stimulation event, a waveform that indicates atrial contraction and traversal of electrical impulse through the A-V node is recorded. Then, the Atrium-Hision (A-H) interval, which is a time interval between atrial contraction and traversal of the electrical impulse through the A-V node upon applying the extra-stimulus pulse, is measured for each stimulation event. Presently, the A-H interval is measured manually by placing horizontal calipers on the waveform. This may be a time consuming affair and lead to inaccurate measurement of A-H intervals. Moreover, a physician may manually determine whether A-H jump is present by comparing A-H intervals corresponding to consecutive stimulation events. For example, the physician may determine that the A-H jump is present if the difference in the A-H intervals is greater than 50 ms. Due to inaccurate A-H intervals, the physician may not be able to precisely detect presence of A-H jump. It is also cumbersome to detect A-H jump as a physician needs to iteratively carry out stimulation events until an A-H jump is detected or satisfactory results are obtained.

SUMMARY

In light of the above, there exists a need to evaluate A-V conduction in a heart through automatic computation of A-H intervals for different stimulation events and determination of A-H jump based on the A-H intervals.

Evaluating Atrio-Ventricular (A-V) conduction in a heart is disclosed. According to one embodiment, a method of evaluating A-V conduction in a heart includes receiving signal data sensed from the heart during an atrial stimulation of the heart, and computing an Atrium-Hision (A-H) interval corresponding to an extra-stimulus event during the atrial stimulation of the heart using the sensed signal data. For example, the sensed signal data may include $RA_{proxy}$ signal, $RA_{distal}$ signal, $His_{proxy}$ signal, $His_{distal}$ signal, $RV_{proxy}$ signal, $RV_{distal}$ signal and an electro-cardiogram (ECG) signal. Furthermore, the method includes determining a difference between the A-H interval corresponding to the extra-stimulus event and an A-H interval corresponding to a preceding extra-stimulus event. Moreover, the method includes automatically determining a presence of an A-H jump based on the determined difference. Additionally, the method may include generating an alert indicating that the presence of the A-H jump.

Therein, the difference between the A-H interval corresponding to the extra-stimulus event and the A-H interval corresponding to the preceding extra-stimulus event is determined by subtracting the computed A-H interval corresponding to the extra-stimulus event from the AH interval corresponding to the preceding extra-stimulus event.

Therein, in determining the presence of the A-H jump based on the determined difference, the method may include computing a difference in pacing cycle lengths at which extra-stimulus pulses associated with the extra-stimulus event and the previous extra-stimulus event respectively are applied to the heart. Furthermore, the method may include determining whether the computed difference in the pacing cycle lengths is within a pre-defined threshold range. If the difference in the pacing cycle lengths is within the pre-defined threshold range, the method may include determining whether the determined difference between the A-H intervals is greater than a pre-determined threshold value. If the determined difference between the A-H intervals is greater than the pre-determined threshold value, the method may include detecting the presence of the A-H jump, where the presence of the A-H jump indicates that the individual is suffering from an Atrial-Ventricular Nodal Reentry Tachycardia (AVNRT) condition.

Therein, in computing the A-H interval corresponding to the extra-stimulus event, the method may include determining a first time value at which extra-stimulus pulse associated with the extra-stimulus event is applied during the atrial simulation of the heart. Furthermore, the method may include determining a second time value at which a P-wave in an electro-cardiogram (ECG) signal corresponding to the extra-stimulus event ends. Moreover, the method may include detecting atrial deflection of at least one His signal corresponding to the extra-stimulus event between the first time value and the second time value. Also, the method may include determining a third time value at which the atrial deflection of the His signal is detected. The method may further include detecting ventricular deflection of a Right Ventricle (RV) signal corresponding to the extra-stimulus event after the second time value, and determining a fourth time value at onset of the ventricular deflection of the RV signal. Furthermore, the method may include detecting His deflection of the His signal between the second time value and the fourth time value, determining a fifth time value at which the His deflection of the His signal is detected, and computing the A-H interval corresponding to the extra-stimulus event based on the third time value and the fifth time value. The A-H interval is a time interval between the third time value and the fifth time value.

In another embodiment, an evaluation device includes a processor, a communication interface coupled to the processor, and a memory coupled to the processor. The memory includes an A-H interval computation module, and an A-H jump determination module. The communication interface is configured for receiving signal data sensed from a heart during an atrial stimulation of the heart. The A-H interval computation module is configured for computing an Atrium-Hision (A-H) interval corresponding to an extra-stimulus event during the atrial stimulation of the heart using the sensed signal data. The A-H jump determination module is configured for determining a difference between the A-H interval corresponding to the extra-stimulus event and an A-H interval corresponding to a preceding extra-stimulus event. Also, the A-H jump determination module is configured for automatically determining presence of an A-H jump based on the determined difference. The memory may further include an alert module configured for generating an alert indicating that the presence of the A-H jump.

Therein, in determining the difference between the A-H intervals, the A-H jump determination module is configured for subtracting the computed A-H interval corresponding to the extra-stimulus event from the AH interval corresponding to the preceding extra-stimulus event.

Therein, in determining the presence of the A-H jump based on the determined difference, the A-H jump determination module is configured for computing a difference in pacing cycle lengths at which extra-stimulus pulses associated with the extra-stimulus event and the previous extra-stimulus event respectively are applied to the heart. Further, the A-H jump determination module is configured for determining whether the computed difference in the pacing cycle lengths is within a pre-defined threshold range. If the difference in the pacing cycle lengths is within the pre-defined threshold range, the A-H jump determination module is configured for determining whether the determined difference between the A-H intervals is greater than a pre-determined threshold value. If the determined difference between the A-H intervals is greater than the pre-determined threshold value, the A-H jump determination module is configured for detecting the presence of the A-H jump, where the presence of the A-H jump indicates that the individual is suffering from an Atrial-Ventricular Nodal Reentry Tachycardia (AVNRT) condition.

Therein, in computing the A-H interval corresponding to the extra-stimulus event, the A-H interval computation module is configured for determining a first time value at which extra-stimulus pulse associated with the extra-stimulus event is applied during the atrial simulation of the heart, and determining a second time value at which P-wave in an electro-cardiogram (ECG) signal corresponding to the extra-stimulus event ends. Furthermore, the A-H interval computation module is configured for detecting atrial deflection of at least one His signal corresponding to the extra-stimulus event between the first time value and the second time value, and determining a third time value at which the atrial deflection of the His signal is detected. Also, the A-H interval computation module is configured for detecting ventricular deflection of a Right Ventricle (RV) signal corresponding to the extra-stimulus event after the second time value, and determining a fourth time value at onset of the ventricular deflection of the RV signal. Moreover, the A-H interval computation module is configured for detecting His deflection of the His signal between the second time value and the fourth time value, and determining a fifth time value at which the His deflection of the His signal is detected. Thereafter, the A-H interval computation module is configured for computing the A-H interval corresponding to the extra-stimulus event based on the third time value and the fifth time value.

In yet another embodiment, a non-transitory computer-readable storage medium has machine-readable instructions stored therein, that when executed by a processor, causes the processor to perform method steps described above.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE VIEWS OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Evaluating atrio-ventricular conduction in a heart is disclosed. Various embodiments are described with reference to the drawings, wherein like reference numerals are used to refer to like elements throughout. In the following description, numerous specific details are set forth in order to provide thorough understanding of embodiments of the present disclosure. It will be apparent, however, to one skilled in the art, that these specific details need not be employed to practice embodiments of the present disclosure. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

Figure 1:
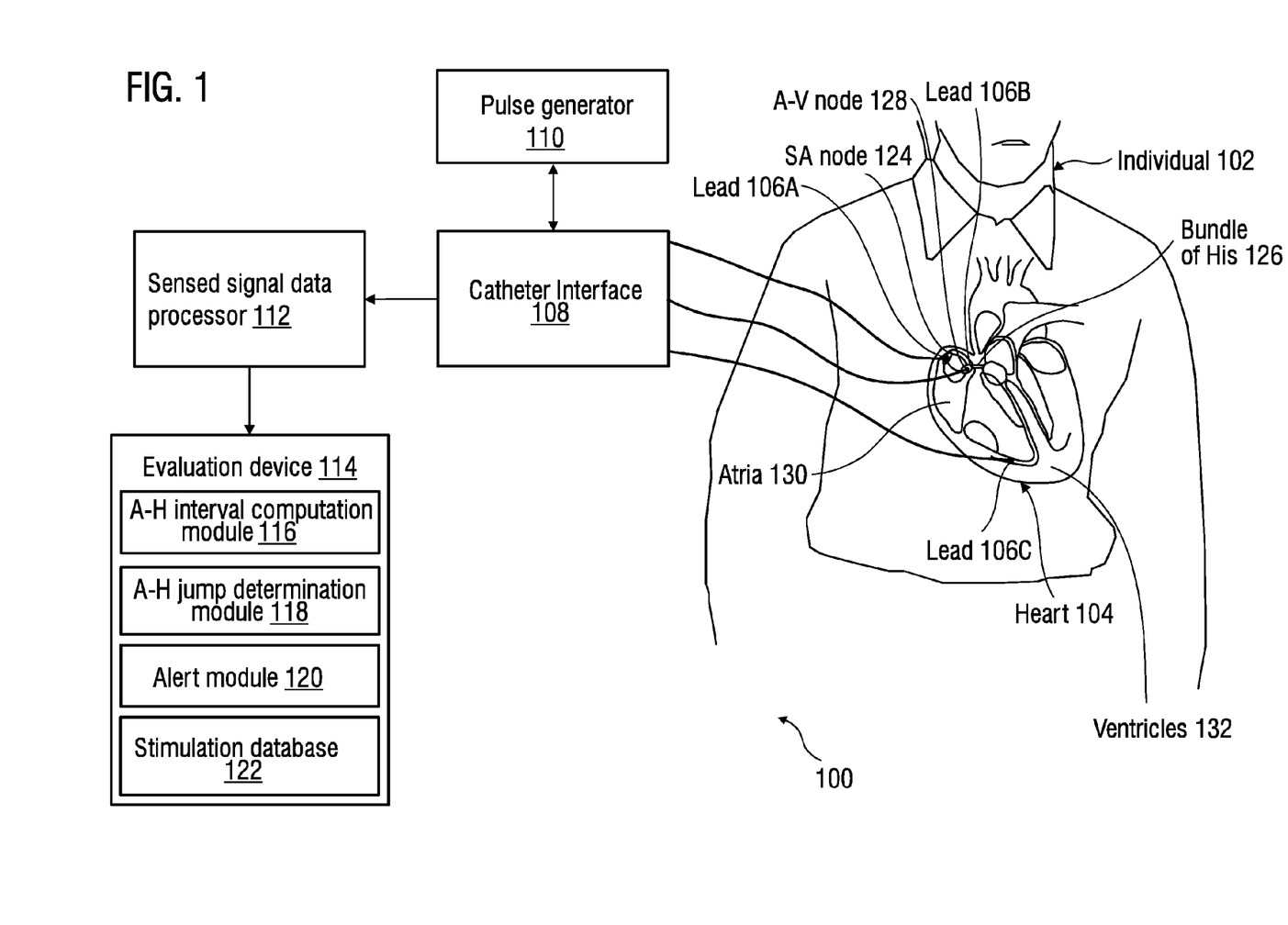
FIG. 1 illustrates a block diagram of one embodiment of a system for evaluating Atrio-Ventricular (A-V) conduction in a heart of an individual.

FIG. 1 illustrates a block diagram of a system 100 for evaluating A-V conduction in a heart 104 of an individual 102, according to one embodiment. The system 100 includes a plurality of leads 106A-C, catheter interface 108, pulse generator 110, sensed data processor 112, and evaluation device 114.

The leads 106A-C combine sensing and pacing electrodes. Lead 106A is in contact with excitable heart tissue in a high right atrium (close to Sinu-Artial Node (SA) node 124) of the heart 104. Lead 106A is capable of sensing electrical impulse generated by the SA node 124 prior to atrial stimulation. Also, lead 106A is capable of stimulating the heart 104 with a series of pulses. Lead 106B is in contact with excitable heart tissue in a bundle of His 126. Lead 106B is capable of sensing contraction of the atrium 130 in response to the stimulation of the HRA and electrical impulse passing through the A-V node 128. Lead 106C is in contact with excitable heart tissue in a right ventricle 132. Lead 106C is capable of contraction of the ventricles 132 in response to the stimulation of the HRA.

The catheter interface 108 is connected to the leads 106A-C. The catheter interface 108 receives sensed data from the leads 106A-C and sends the series of pulses to the lead 106A during stimulation of the HRA. The pulse generator 110 is connected to lead 106A via the catheter interface 108. The pulse generator 110 is capable of generating one or more series of pulses for stimulating the atrium 130 via lead 106A. For example, the pulse generator 110 is pre-configured to generate a series of pulses having a same pacing cycle length followed by an extra-stimulus pulse with a different pacing cycle length during each stimulation event. For example, the pacing cycle length of the series of pulses may range from 150 milliseconds (ms) to 600 ms. The pacing cycle length of the extra-stimulus pulse at the end of the stimulation event is less than the pacing cycle length of the series of pulses preceding the extra-stimulus event. Furthermore, the pulse generator 110 is pre-configured to generate extra-stimulus pulses with different pacing cycle lengths during subsequent stimulation events. For example, the pulse generator 110 is pre-configured to reduce pacing cycle length of the extra-stimulus pulse by 10-20 ms for each subsequent stimulation event. Alternatively, the pulse generator 110 may be pre-configured to increase the pacing cycle length of the extra-stimulus pulse for each subsequent stimulation event. It can be noted that the pulse generator 110 may generate pulses for stimulating the HRA in response to electrical impulses generated by the SA node 124 (sensed by the lead 106A).

The sensed signal data processor 112 is connected to the catheter interface 108. The sensed data processor 112 is configured to convert the sensed signal data in analog form to digital form. The sensed signal data may include $RA_{proxy}$ signal, $RA_{distal}$ signal, $His_{proxy}$ signal, $His_{distal}$ signal, $RV_{proxy}$ signal, $RV_{distal}$ signal, etc. corresponding to each stimulation event. For example, these signals indicate contraction and expansion of atria and ventricles in response to each stimulation event.

As described earlier, a plurality of stimulation events are carried out during the atrial stimulation of the heart 104 in order to evaluate the A-V conduction in the heart 104. During each stimulation event, a series of pulses (synchronous pulses) followed by extra-stimulus pulse (asynchronous pulse) is applied via lead 106A by pulse generator 110. Consequently, the leads 106A-C sense depolarization and repolarization of the atria 130 and ventricles 132 in response to said each stimulation event and provide the sensed signal data in the form of $RA_{proxy}$ signal, $RA_{distal}$ signal, $His_{proxy}$ signal, $His_{distal}$ signal, $RV_{proxy}$ signal, $RV_{distal}$ signal, etc. to the sensed signal data processor 112 via the catheter interface 108. These signals indicate deflections with respect to time.

As depicted, the evaluation device 114 is connected to the sensed signal data processor 112. The evaluation device 114 is configured to evaluate A-V conduction in the heart 104 based on the sensed signal data in the digital form. The evaluation device 114 includes A-H interval computation module 116, A-H jump determination module 118, alert module 120, and stimulation database 122.

During the atrial simulation, the evaluation device 114 receives the sensed signal data corresponding to each stimulation event in digital form from the sensed data processor 112. The evaluation device 114 stores the sensed signal data corresponding to each stimulation event in the simulation database 122. The stimulation database 122 also stores the pacing cycle length associated with the series of pulses and the pacing cycle length of extra-stimulus pulse applied during each extra-stimulus event. The stimulation database 122 stores the time at which the extra-stimulus pulse is applied during each stimulation event. Additionally, the stimulation database 122 stores an Electro-cardiogram (ECG) signal of the heart 104 captured during said each stimulation event.

The A-H interval computation module 116 computes an A-H interval during the extra-stimulus event based on the sensed signal data received from the sensed signal data processor 112. The A-H interval is the time duration between first rapid contraction of the atria 130 and traversal of electrical impulse through the A-V node 126 upon applying the extra-stimulus pulse to the HRA during the stimulus event. The first rapid contraction of the atria 130 is represented by an atrial deflection of at least one His signal from a bundle of His signals. Typically, the atrial deflection of the His signal is observed after applying the extra-stimulus pulse and before the end of 'P' wave of an ECG corresponding to the extra-stimulus event. Similarly, the electrical impulse passing through the A-V node 126 is represented by His deflection of the at least one His signal prior to first rapid contraction of the ventricles 132. For computing the A-H interval, the A-H interval computation module 116 determines the atrial deflection and the His deflection in the bundle of His signals. Then, the A-H interval computation module 116 determines the time at which the atrial deflection and the His deflection of the at least one His signal occurred. The A-H interval computation module 116 computes the time interval between the time at which the atrial deflection and the time at which the His deflection occurred. The computed time interval is the A-H interval for the extra-stimulus event. In this manner, the A-H interval computation module 116 computes A-H interval for each stimulation event and stores the A-H interval in the stimulation database 122. The process of computing the A-H interval is explained in greater detail in FIG. 3.

The A-H jump determination module 118 compares the A-H interval computed for the extra-stimulus event with an A-H interval computed for preceding extra-stimulus event. The extra-stimulus event and the preceding extra-stimulus event correspond to different stimulation events. The stimulation events may be consecutive events or non-consecutive events carried out during the atrial stimulation. The A-H jump determination module 118 determines whether there is a presence of the A-H jump based on the difference between the A-H intervals. For example, the A-H jump is said to be present when the difference between the A-H intervals is greater than 50 ms. The A-H jump is generally detected when there is improper A-V conduction in the heart. In other words, the A-H jump is detected when there is leakage of electricity while passing through the A-V node 128. Thus, the presence of the A-H jump indicates that the individual is likely to suffer from cardiac arrhythmia, such as an Atrio-Ventricular Nodal Reentry Tachycardia (AVNRT) condition.

The alert module 120 generates an alert indicating the presence of the A-H jump. The alert module 120 may display the alert on a display of the evaluation device 114. Alternatively, the alert module 120 may generate an alarm sound to indicate that the A-H jump is detected. In this manner, the evaluation device 114 automatically detects the presence of the A-H jump during the atrial stimulation of the heart 104 and alerts a physician conducting the atrial simulation regarding the A-H jump. Thus, the need for manually computing the A-H intervals and determining whether there is A-H jump or not is eliminated. Thus, accuracy of the A-H interval is significantly improved and time required for manually calculating the A-H intervals is saved.

Although in FIG. 1, the catheter interface 108, the pulse generator 110, the sensed signal data processor 112, and the evaluation device 114 are shown as independent units, however, the catheter interface 108, the pulse generator 110, the sensed signal data processor 112 can be part of the evaluation device 114, and the leads 106A-C can be directly connected to the evaluation device 114.

Figure 2:
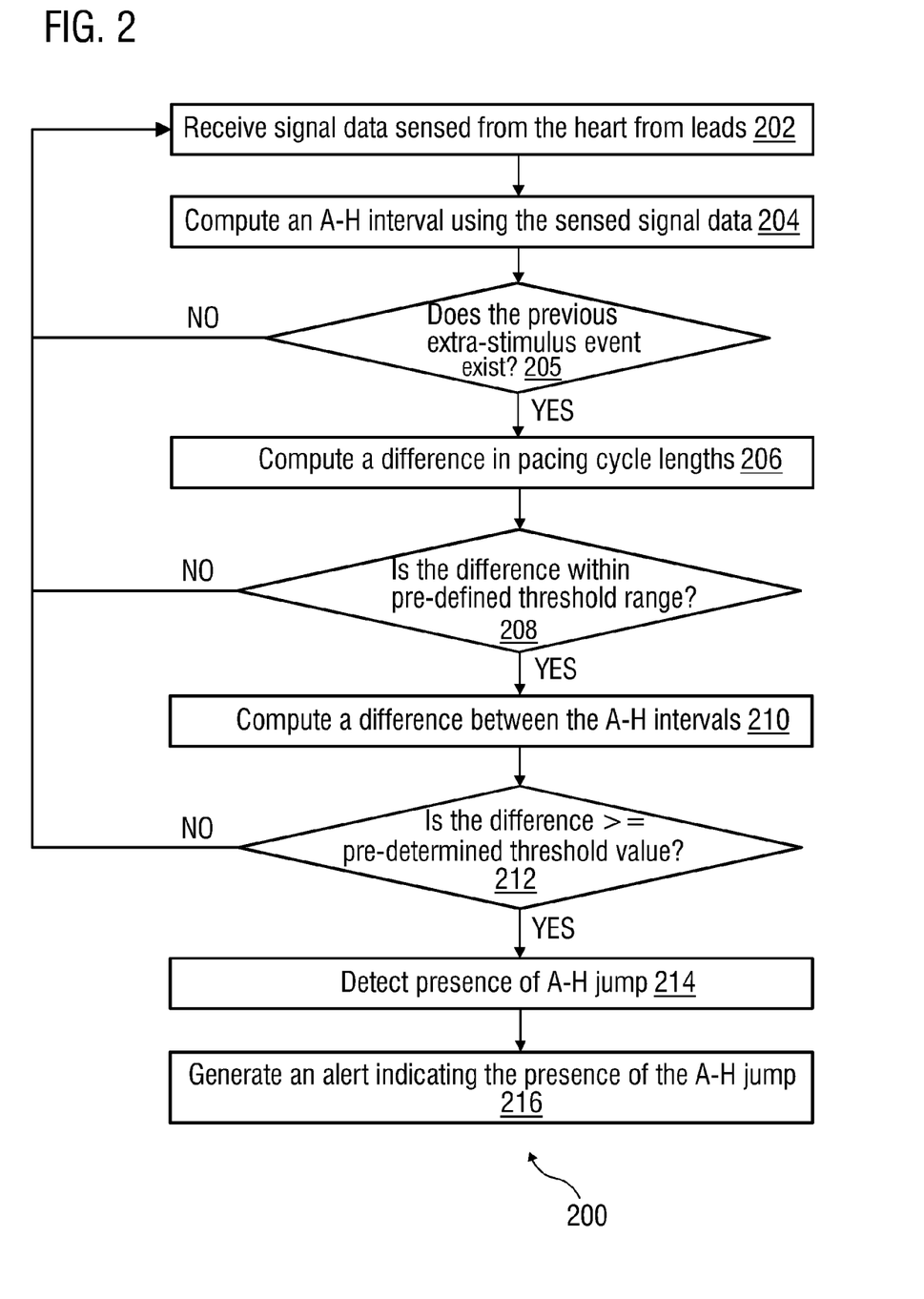
FIG. 2 illustrates an exemplary method of evaluating A-V conduction in the heart of the individual.
Figure 4:
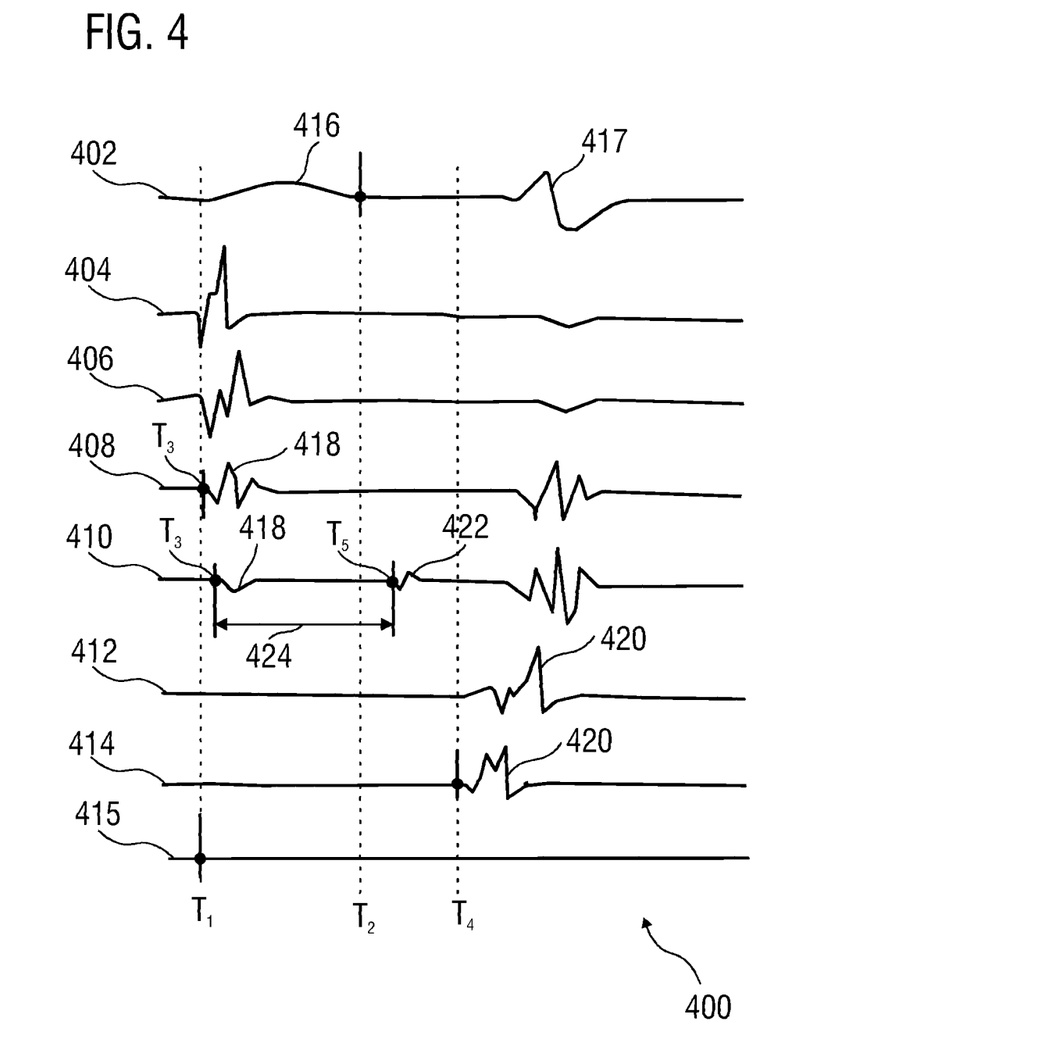
FIG. 4 illustrates a schematic representation depicting example computation of an A-H interval for an extra-stimulus event using sensed signal data.

FIG. 2 illustrates an exemplary method 200 of evaluating A-V conduction in a heart 104 of the individual 102, according to one embodiment. At step 202, signal data sensed from the heart 104 during an atrial stimulation of the heart 104 is received from leads 106A-C. For example, the signal data is sensed by leads 106A-C in response to the stimulation event applied to HRA. The signal data represents contraction and expansion of the atria 130 and the ventricles 132 in response to application of series of pulses followed by an extra-stimulus pulse during the stimulation event. The signal data corresponds to $RA_{proxy}$ signal, $RA_{distal}$ signal, $His_{proxy}$ signal, $His_{distal}$ signal, $RV_{proxy}$ signal, $RV_{distal}$ signal and an ECG signal. These signals, which correspond to extra-stimulus event, are illustrated in FIG. 4. The sensed signal data is received after each stimulation event during the atrial stimulation. In case the sensed signal data is in analog form, it is converted into a digital form using signal data processor 112. The sensed signal data in the digital form is then stored in the stimulation database 122.

At step 204, an A-H interval corresponding to an extra-stimulus event associated with the stimulation event is computed using the sensed signal data for the extra-stimulus event. For example, the A-H interval is computed for the extra-stimulus event as the extra-stimulus pulse is has a different pacing cycle length compared to series of pulses applied during the stimulation event. This would help for accurate evaluation of A-V conduction in the heart 104. The process steps involved in computing the A-H interval are explained in greater detail in FIG. 3.

At step 205, it is determined whether an extra-stimulus event preceding the current extra-stimulus event exists. For example, there may be no preceding extra-stimulus event if the stimulus event is a first stimulus event of the atrial stimulation. If the preceding extra-stimulus event does not exist, the process 200 is routed back to the step 202.

If the preceding extra-stimulus event exists, then at step 206, a difference in pacing cycle lengths at which extra-stimulus pulses associated with the current extra-stimulus event and the preceding extra-stimulus event respectively are applied to the heart 104 is computed. The current extra-stimulus event and the preceding extra-stimulus event correspond to different stimulus events and have different pacing cycle lengths. At step 208, it is determined whether the difference in the pacing cycle lengths is within a pre-defined threshold range. For example, the pre-defined threshold range may be equal to 10 ms to 20 ms.

If the difference in the pacing cycle lengths falls outside the pre-defined threshold range, then the process is routed back to step 202. Otherwise step 210 is performed. At step 210, a difference between the A-H interval for the current extra-stimulus event and an A-H interval for a preceding extra-stimulus event is computed. In an exemplary embodiment, the computed A-H interval is subtracted from the A-H interval for the preceding extra-stimulus event. At step 212, it is determined whether the difference in the A-H intervals is greater than or equal to a pre-determined threshold value. For example, the pre-determined threshold value may be equal to 50 ms. One skilled in the art may realize that the pre-determined threshold value may be any value other than 50 ms. If the difference in the A-H intervals is less than the pre-determined threshold value, then the process 200 is routed back to step 202.

If the difference in the A-H intervals is greater than or equal to the pre-determined threshold value, then at step 214, the A-H jump is considered as present. For example, the A-H jump is associated with an AVNRT condition in an individual. In other words, the presence of A-H jump indicates that the individual 102 is suffering from the AVNRT condition. At step 216, an alert indicating presence of A-H jump is generated. The alert may be an alarm sound or notification displayed on a graphical user interface. In this manner, the A-V conduction in the heart is evaluated by automatically identifying presence of A-H jump and alerting a physician regarding the presence of the A-H jump.

Figure 3:
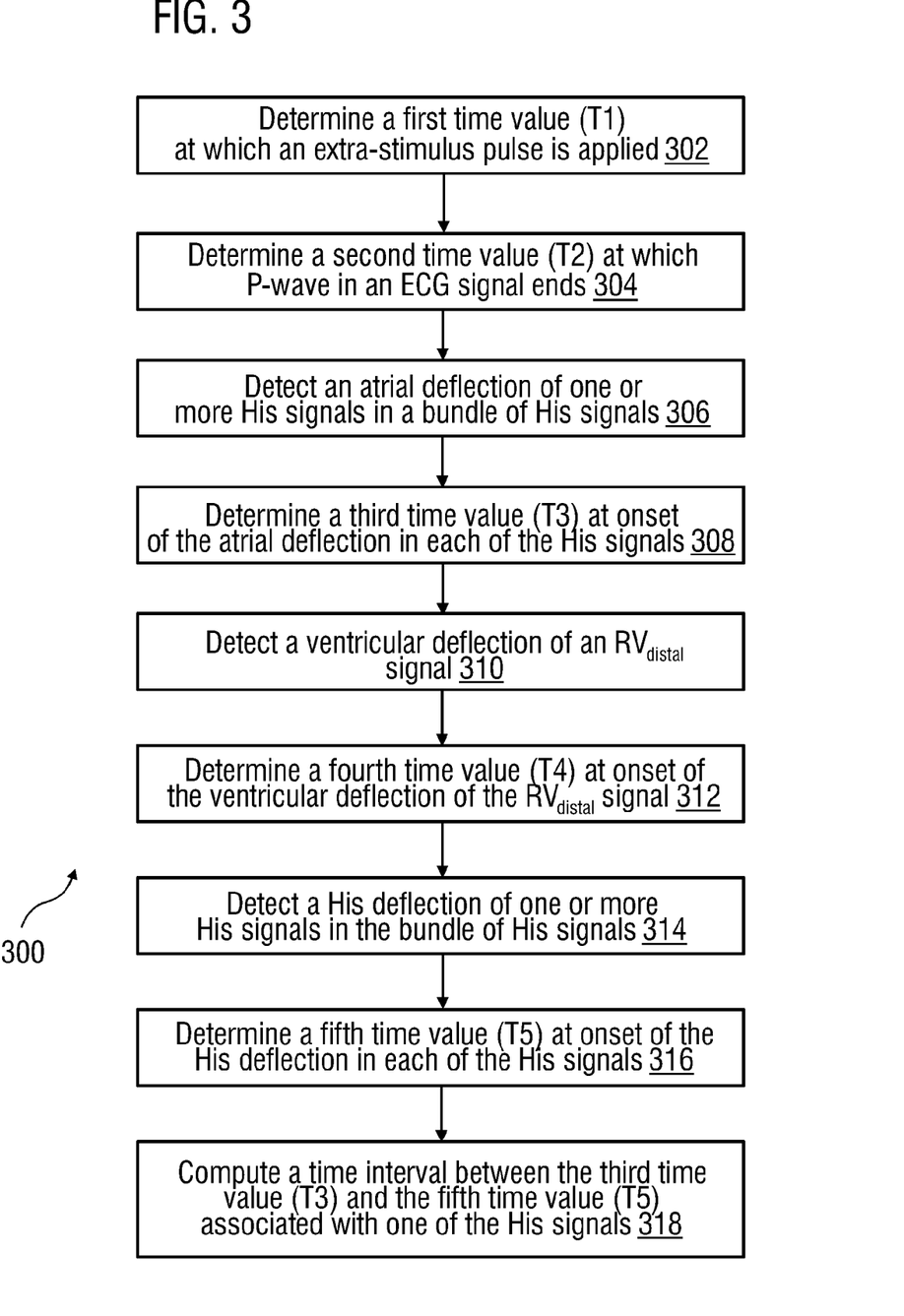
FIG. 3 illustrates an exemplary method of computing Atrium-Hision (A-H) interval for an extra-stimulus event associated with a stimulation event.

FIG. 3 illustrates an exemplary method 300 of computing the A-H interval for the extra-stimulus event associated with the stimulation event, according to one embodiment. It may be noted that the process steps 302 to 318 are performed for computing the A-H interval in step 204 in FIG. 2. According to the present embodiment, the A-H interval is computed using the signal data sensed in response to application of extra-stimulus pulse following a series of pulses during a stimulation event. In this embodiment, the A-H interval is computed based on atrial deflection and the His deflection of a bundle of His signals recorded in response to the extra-stimulus pulse.

At step 302, a first time value (T1) at which an extra-stimulus pulse corresponding to the extra-stimulus event is applied during a stimulation event is determined. For example, the extra stimulus pulse is searched in a stimulation waveform associated with the stimulation event. Then, the first time value (T1) at onset of the extra-stimulus pulse is determined. At step 304, a second time value (T2) at which the P-wave in an ECG signal corresponding to the extra-stimulus event ends is determined. For example, a point which indicates the end of the P-wave is searched in the ECG signal. Thereafter, the second time value (T2), at which the P-wave ends, is determined based on the point in the ECG signal.

At step 306, an atrial deflection of one or more His signals in a bundle of His signals is detected. For example, the atrial deflection is searched in each of the His signals between the first time value (T1) and the second time value (T2). The possibility of atrial deflection between the first time value (T1) and the second time value (T2) is high as atrial contraction occurs after applying the extra-stimulus pulse and before the end of P-wave in the ECG signal. Once the atrial deflection is detected in the one or more His signals, at step 308, a third time value (T3) at onset of the atrial deflection in each of the His signals is determined. For example, the third time value (T3) at the onset of the atrial deflection in the $His_{distal}$ signal and the $His_{proxy}$ signal is determined.

At step 310, a ventricular deflection of an $RV_{distal}$ signal is detected. For example, the $RV_{distal}$ signal is searched for the ventricular deflection after the second time value (T2). At step 312, a fourth time value (T4) at the onset of the ventricular deflection of the $RV_{distal}$ signal is determined. The fourth time value (T4) is the time at which ventricular contraction takes place.

At step 314, a His deflection of one or more His signals in the bundle of His signals is detected. For example, the His deflection is searched in each of the His signals between the second time value (T2) and the fourth time value (T4). The possibility of the His deflection between the second time value (T2) and the fourth time value (T4) is high as electrical impulse traverses through the A-V node 128 after the atrial contraction (i.e., after the end of P-wave) and before the ventricular contraction (before the ventricular deflection of the $RV_{distal}$ signal). Once the His deflection is detected in the one or more His signals, at step 316, a fifth time value (T5) at the onset of the His deflection in each of the His signals is determined. For example, the fifth time value (T5) at the onset of the His deflection in the $His_{distal}$ signal, and the $His_{proxy}$ signal is determined.

At step 318, a time interval between the third time value (T3) and the fifth time value (T5) associated with one of the His signals is computed. For example, it is determined whether the third time value (T3) and the fifth time value (T5) exist for the $His_{distal}$ signal. If so, the third time value (T3) and the fifth time value (T5) are used for computing the time interval. This computed time interval is nothing but the A-H interval corresponding to the extra-stimulus pulse applied to the HRA during the stimulation event. If the third time value (T3) and the fifth time value (T5) do not exist for the $His_{distal}$ signal, the $His_{proxy}$ signal is selected for computing the A-H interval. If the third time value (T3) and the fifth time value (T5) do not exist for the $His_{proxy}$ signal, it is determined whether any other His signal is considered for computing the A-H interval. If no other His signal is available, then the A-H interval is not calculated and an alert indicating that no A-H interval can be computed is generated.

FIG. 4 is a schematic representation 400 depicting computation of an A-H interval for an extra-stimulus event using sensed signal data. As shown in FIG. 4, the sensed signal data 400 includes an ECG signal 402, $RA_{proxy}$ signal 404, $RA_{distal}$ signal 406, $His_{proxy}$ signal 408, $His_{distal}$ signal 410, $RV_{proxy}$ signal 412, and $RV_{distal}$ signal 414 as recorded after applying signal extra-stimulus event 415 to the HRA. The ECG signal 402 contains a P-wave 416 indicative of contraction of atria and a QRS wave 417 indicative of contraction of ventricles. The $RA_{proxy}$ signal 404 and the $RA_{distal}$ signal 406 indicate contraction of the atria 130 at proximal end and distal end from the SA node 124. The $His_{proxy}$ signal 408 and $His_{distal}$ signal 410 indicate contraction of the atria 130 and traversal of electrical impulse through the bundle of His 126 in response to the extra-stimulus pulse 415. The $RV_{proxy}$ signal 412 and the $RV_{distal}$ signal 414 indicate contraction of ventricles 132 at proximal end and distal end.

As described earlier, contraction of the atria 130 takes place after time T1 at which the extra-stimulus event 415 is applied and prior to time T2 at which the P-wave 416 ends. An atrial deflection 418 can be seen on bundle of His signals 408 and 410 between the time T1 and the time T2. Once the atrial deflection 418 is identified on the bundle of His signals 408 and 410, onset time T3 at which the atrial deflection 418 is seen on the bundle of His signals 408 and 410 is determined. As can be seen, the onset time T3 lies between the time T1 and the time T2 on the $His_{proxy}$ signal 408 and the $His_{distal}$ signal 410.

Post atrial contraction, the electrical impulse passes through the A-V node 128 and then through the bundle of His 126 before stimulating cardiac muscle of the ventricles 132, resulting in contraction of the ventricles 132. When the right ventricle 132 contracts due to stimulation by the electrical impulse, ventricular deflection 420 can be seen on the RV signals 412 and 414. Once the ventricular deflection 420 is identified, the time T4 at onset of the ventricular deflection 420 is determined from the $RV_{distal}$ signal 414.

It is known that the electrical impulse travels through the A-V node 128 after the atrial contraction (at time T2) and prior to the ventricular contraction (at time T4). Thus, the event of traversal of the electrical impulse through the A-V node 128 would normally occur between the time T2 and the time T4. The event of traversal of the electrical impulse can be seen as His deflection 422 on the bundle of His signals 408 and 410 between the time T2 and the time T4. It can be seen that the His deflection 422 occurs on the $His_{distal}$ signal 410 and not on the $His_{proxy}$ signal 408. Once the His deflection 422 is identified, the onset time T5 at which the His deflection 422 is seen on the $His_{distal}$ signal 410 is also determined. Accordingly, based on the $His_{distal}$ signal parameters, the A-H interval 424 is computed as a time interval between the time T3 and the time T5 associated with the atrial deflection 418 and the His deflection 420 of the $His_{distal}$ signal 410. Thus, the A-H interval 424 is automatically computed based on sensed signal data recorded for the extra-stimulus pulse following series of pulses during each stimulation event.

Figure 5:
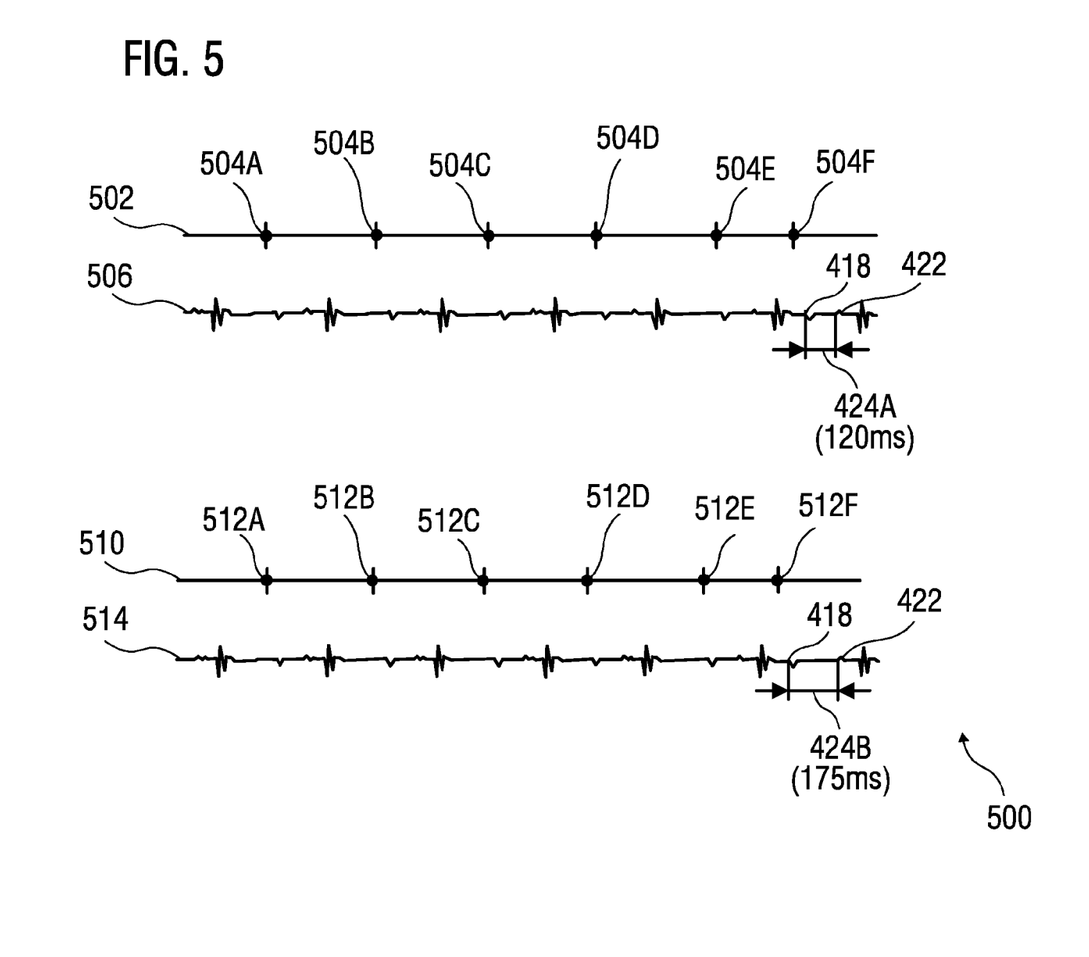
FIG. 5 is a schematic representation depicting an example A-H jump detection by comparing A-H intervals associated with consecutive stimulation events.

FIG. 5 is a schematic representation 500 depicting A-H jump detection by comparing A-H intervals associated with consecutive stimulation events. Consider that, during a first stimulation event 502, the HRA is stimulated with five pulses 504A-E with pacing cycle length of 600 ms followed by an extra-stimulus pulse 504F with pacing cycle length 300 ms. A $His_{distal}$ signal 506 recorded during the stimulation event 502 is depicted in FIG. 5. It can be seen from the $His_{distal}$ signal 506 that A-H interval 424A corresponding to the extra-stimulus pulse 504F is computed automatically as 120 ms in the manner mentioned in FIG. 4.

Now consider that during a second stimulation event 510, the HRA is stimulated with pulses 512A-E with pacing cycle length of 600 ms followed by an extra-stimulus pulse 512F with pacing cycle length of 290 ms. The $His_{distal}$ signal 514 recorded during the stimulation event 510 is depicted in FIG. 5. Consider that an A-H interval 424B equal to 175 ms is computed automatically as described in FIG. 4 for the extra-stimulus pulse 512F applied during the second stimulation event 510. It can be seen that the pacing cycle length of the extra-stimulus pulse 512F is less than the extra-stimulus pulse 504F. The evaluation device 114 computes the a difference between the A-H intervals 424A and 424B is 55 ms, which is greater than threshold value of 50 ms. Accordingly, the evaluation device 114 automatically determines presence of A-H jump (difference in A-H intervals>50 ms) and alerts a physician regarding the A-H jump. For example, in some patients, the value of the A-H jump equal to 55 ms indicates that the individual 102 is suffering from AVNRT condition.

Figure 6:
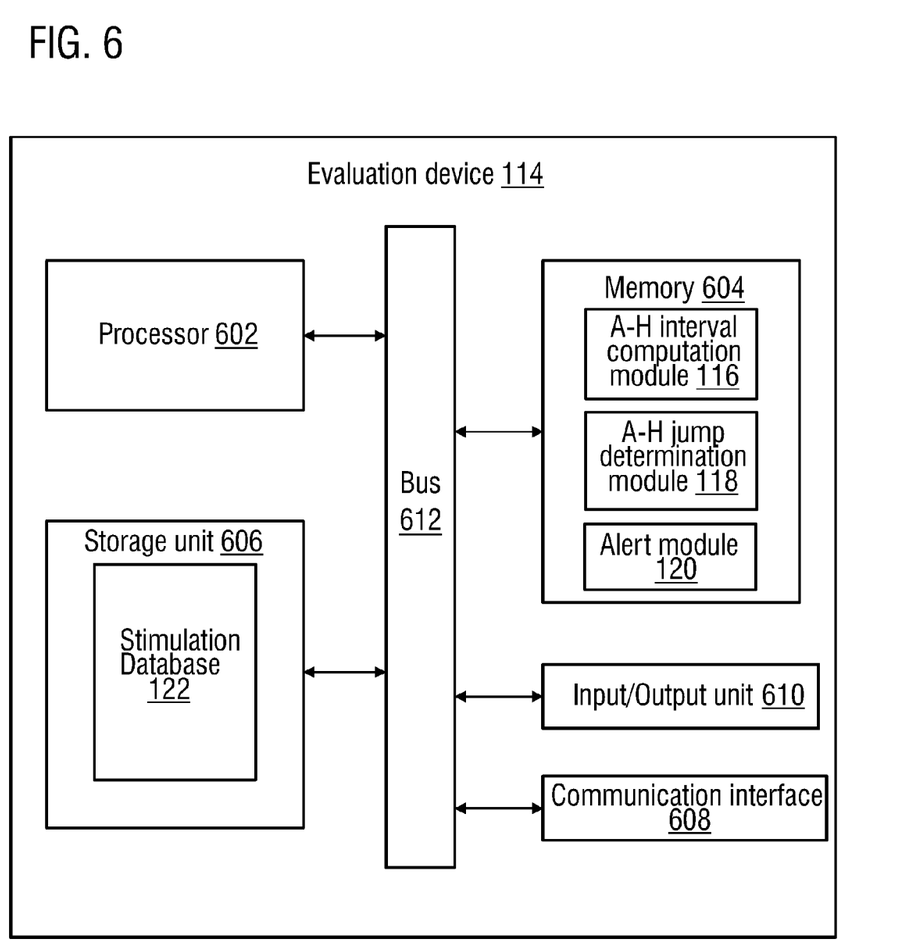
FIG. 6 illustrates a block diagram of an evaluation device such as those shown in FIG. 1 according an embodiment.

FIG. 6 illustrates a block diagram of the evaluation device 114 shown in FIG. 1 according one embodiment. The evaluation device 114 may be a personal computer, a laptop computer, a tablet, a health monitoring device and the like. In FIG. 6, the evaluation device 114 includes a processor 602, memory 604, storage unit 606, communication interface 608, input/output unit 610, and bus 612.

Processor 602, as used herein, is any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. Processor 602 may also include embedded controllers, such as generic or programmable logic devices or arrays, application specific integrated circuits, single-chip computers, and the like.

Memory 604 may be volatile memory and non-volatile memory. The memory 604 may be coupled for communication with processor 602. Processor 602 may execute instructions and/or code stored in memory 604. A variety of computer-readable storage media may be stored in and accessed from memory 604. Memory 604 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, memory 604 includes the A-H interval computation module 116, the A-H jump determination module 118 and the alert generation module 120 stored in the form of machine-readable instructions on any of the above-mentioned storage media and may be in communication to and executed by processor 602. The functionalities of the modules 116 to 120, when executed by the processor 602, are already described in greater in FIG. 1.

The storage unit 606 may be a non-transitory storage medium which stores the stimulation database 122. The communication interface 608 enables the evaluation device 114 to communicate with the sensed signal data processor 112 via wired or wireless communication protocol known in the art. The input/output unit 610 may include input means such as keypad, touch-sensitive display, etc. capable of receiving input signal, and output means such as speaker, printer, display means for outputting output signal such as alert indicating presence of A-H jump. The bus 612 acts as interconnect between processor 602, memory 604, storage unit 606, communication interface 608, and input/output unit 610.

It is to be understood that the system and methods described herein may be implemented in various forms of hardware, software, firmware, special purpose processors, or a combination thereof. One or more of the present embodiments may take a form of a computer program product comprising program modules accessible from computer-usable or computer-readable medium storing program code for use by or in connection with one or more computers, processors, or instruction execution system. For the purpose of this description, a computer-usable or computer-readable medium can be any apparatus that can contain, store, communicate, propagate, or transport the program for use by or in connection with the instruction execution system, apparatus, or device. The medium can be electronic, magnetic, optical, electromagnetic, infrared, or semiconductor system (or apparatus or device) or a propagation mediums in and of themselves as signal carriers are not included in the definition of physical computer-readable medium include a semiconductor or solid state memory, magnetic tape, a removable computer diskette, random access memory (RAM), a read only memory (ROM), a rigid magnetic disk and optical disk such as compact disk read-only memory (CD-ROM), compact disk read/write, and DVD. Both processors and program code for implementing each aspect of the technology can be centralized or distributed (or a combination thereof) as known to those skilled in the art.

While the present disclosure has been described in detail with reference to certain embodiments, it should be appreciated that the present disclosure is not limited to those embodiments. In view of the present disclosure, many modifications and variations would be present themselves, to those skilled in the art without departing from the scope of the various embodiments of the present disclosure, as described herein. The scope of the present disclosure is, therefore, indicated by the following claims rather than by the foregoing description. All changes, modifications, and variations coming within the meaning and range of equivalency of the claims are to be considered within their scope.

What is claimed is:

1. A method of evaluating Atrial-Ventricular (A-V) conduction in a heart of an individual, the method comprising:

receiving, from leads, signal data sensed from the heart during an atrial stimulation of the heart, wherein the sensed signal data comprises data associated signals selected from the group consisting of $RA_{proxy}$ signal, $RA_{distal}$ signal, $His_{proxy}$ signal, $His_{distal}$ signal, $RV_{proxy}$ signal, $RV_{distal}$ signal and an electro-cardiogram (ECG) signal;

computing, by a processor, an Atrium-Hision (A-H) interval corresponding to an extra-stimulus event during the atrial stimulation of the heart using the sensed signal data;

determining, by the processor, a difference between the A-H interval corresponding to the extra-stimulus event and an A-H interval corresponding to a preceding extra-stimulus event; and automatically determining, by the processor, presence of an A-H jump based on the determined difference and generating an alert indicating the presence of the A-H jump.

2. The method of claim 1, wherein determining the difference between the A-H interval corresponding to the extra-stimulus event and the A-H interval corresponding to the preceding extra-stimulus event comprises:
sub­tracting the computed A-H interval corresponding to the extra-stimulus event from the A-H interval corresponding to the preceding extra-stimulus event.

3. The method of claim 1, wherein determining the presence of the A-H jump based on the determined difference comprises:
computing a difference in pacing cycle lengths at which extra-stimulus pulses associated with the extra-stimulus event and the previous extra-stimulus event respectively are applied to the heart;
determining whether the computed difference in the pacing cycle lengths is within a pre-defined threshold range;
when the difference in the pacing cycle lengths is within the pre-defined threshold range, determining whether the determined difference between the A-H intervals is greater than a pre-determined threshold value; and
when the determined difference between the A-H intervals is greater than the pre-determined threshold value, detecting the presence of the A-H jump.

4. The method of claim 1, wherein computing the A-H interval corresponding to the extra-stimulus event comprises:
determining a first time value at which extra-stimulus pulse associated with the extra-stimulus event is applied during the atrial simulation of the heart;
determining a second time value at which a P-wave in an electro-cardiogram (ECG) signal corresponding to the extra-stimulus event ends;
detecting atrial deflection of at least one His signal corresponding to the extra-stimulus event between the first time value and the second time value;
determining a third time value at which the atrial deflection of the His signal is detected;
detecting ventricular deflection of a Right Ventricle (RV) signal corresponding to the extra-stimulus event after the second time value;
determining a fourth time value at onset of the ventricular deflection of the RV signal;
detecting His deflection of the His signal between the second time value and the fourth time value;
determining a fifth time value at which the His deflection of the His signal is detected; and
computing the A-H interval corresponding to the extra-stimulus event based on the third time value and the fifth time value.

5. The method of claim 4, wherein the A-H interval is a time interval between the third time value and the fifth time value.

6. The method of claim 1, wherein the presence of the A-H jump indicates that the individual is suffering from an Atrial-Ventricular Nodal Reentry Tachycardia (AVNRT) condition.

7. An evaluation device comprising:
a processor;
a communication interface coupled to the processor and configured for receiving signal data sensed from a heart during an atrial stimulation of the heart, wherein the sensed signal data comprises data associated signals selected from the group consisting of $RA_{proxy}$ signal, $RA_{distal}$ signal, $His_{proxy}$ signal, $His_{distal}$ signal, $RV_{proxy}$ signal, $RV_{distal}$ signal and an electro-cardiogram (ECG) signal; and
a memory coupled to the processor, wherein the memory comprises:
an A-H interval computation module configured for computing an Atrium-Hision (A-H) interval corresponding to an extra-stimulus event during the atrial stimulation of the heart using the sensed signal data; and
an A-H jump determination module configured for:
determining a difference between the A-H interval corresponding to the extra-stimulus event and an A-H interval corresponding to a preceding extra-stimulus event; and
automatically determining presence of an A-H jump based on the determined difference and an alert module configured for generating an alert indicating the presence of the A-H jump.

8. The evaluation device of claim 7, wherein in determining the difference between the A-H intervals, the A-H jump determination module is configured for:
subtracting the computed A-H interval corresponding to the extra-stimulus event from the AH interval corresponding to the preceding extra-stimulus event.

9. The evaluation device of claim 7, wherein in determining the presence of the A-H jump based on the determined difference, the A-H jump determination module is configured for:
computing a difference in pacing cycle lengths at which extra-stimulus pulses associated with the extra-stimulus event and the previous extra-stimulus event respectively are applied to the heart;
determining whether the computed difference in the pacing cycle lengths is within a pre-defined threshold range;
when the difference in the pacing cycle lengths is within the pre-defined threshold range, determining whether the determined difference between the A-H intervals is greater than a pre-determined threshold value; and
when the determined difference between the A-H intervals is greater than the pre-determined threshold value, detecting the presence of the A-H jump.

10. The evaluation device of claim 7, wherein in computing the A-H interval corresponding to the extra-stimulus event, the A-H interval computation module is configured for:
determining a first time value at which extra-stimulus pulse associated with the extra-stimulus event is applied during the atrial simulation of the heart;
determining a second time value at which P-wave in an electro-cardiogram (ECG) signal corresponding to the extra-stimulus event ends;
detecting atrial deflection of at least one His signal corresponding to the extra-stimulus event between the first time value and the second time value;
determining a third time value at which the atrial deflection of the His signal is detected;
detecting ventricular deflection of a Right Ventricle (RV) signal corresponding to the extra-stimulus event after the second time value;
determining a fourth time value at onset of the ventricular deflection of the RV signal;
detecting His deflection of the His signal between the second time value and the fourth time value;

determining a fifth time value at which the His deflection of the His signal is detected; and computing the A-H interval corresponding to the extra-stimulus event based on the third time value and the fifth time value.

11. The evaluation device of claim 7, wherein the presence of the A-H jump indicates that the individual is suffering from an Atrial-Ventricular Nodal Reentry Tachycardia (AVNRT) condition.

12. A non-transitory computer-readable storage medium having machine-readable instructions stored therein, that when executed by a processor, the storage medium comprising instructions for:

receiving signal data sensed from a heart during an atrial stimulation of the heart, wherein the sensed signal data comprises data associated signals selected from the group consisting of $RA_{proxy}$ signal, $RA_{distal}$ signal, $His_{proxy}$ signal, $His_{distal}$ signal, $RV_{proxy}$ signal, $RV_{distal}$ signal and an electro-cardiogram (ECG) signal;

computing an Atrium-Hision (A-H) interval corresponding to an extra-stimulus event during the atrial stimulation of the heart using the sensed signal data;

determining a difference between the A-H interval corresponding to the extra-stimulus event and an A-H interval corresponding to a preceding extra-stimulus event; and automatically determining presence of an A-H jump based on the determined difference and generating an alert indicating the presence of the A-H jump.

13. The storage medium of claim 12, wherein in determining the difference between the A-H intervals, the instructions comprise:

subtracting the computed A-H interval corresponding to the extra-stimulus event from the AH interval corresponding to the preceding extra-stimulus event.

14. The storage medium of claim 12, wherein in determining the presence of the A-H jump based on the determined difference, the instructions comprise:

computing a difference in pacing cycle lengths at which extra-stimulus pulses associated with the extra-stimulus event and the previous extra-stimulus event respectively are applied to the heart;

determining whether the computed difference in the pacing cycle lengths is within a pre-defined threshold range;

when the difference in the pacing cycle lengths is within the pre-defined threshold range, determining whether the determined difference between the A-H intervals is greater than a pre-determined threshold value; and when the determined difference between the A-H intervals is greater than the pre-determined threshold value, detecting the presence of the A-H jump.

15. The storage medium of claim 12, wherein in computing the A-H interval corresponding to the extra-stimulus event, the instructions comprising:

determining a first time value at which extra-stimulus pulse associated with the extra-stimulus event is applied during the atrial simulation of the heart;

determining a second time value at which P-wave in an electro-cardiogram (ECG) signal corresponding to the extra-stimulus event ends;

detecting atrial deflection of at least one His signal corresponding to the extra-stimulus event between the first time value and the second time value;

determining a third time value at which the atrial deflection of the His signal is detected;

detecting ventricular deflection of a Right Ventricle (RV) signal corresponding to the extra-stimulus event after the second time value;

determining a fourth time value at onset of the ventricular deflection of the RV signal;

detecting His deflection of the His signal between the second time value and the fourth time value;

determining a fifth time value at which the His deflection of the His signal is detected; and computing the A-H interval corresponding to the extra-stimulus event based on the third time value and the fifth time value.

16. The storage medium of claim 15, wherein the A-H interval is time interval between the third time value and the fifth time value.

* * * * *